United States Patent [19]
Kehoe

[11] Patent Number: 5,794,203
[45] Date of Patent: Aug. 11, 1998

[54] BIOFEEDBACK SYSTEM FOR SPEECH DISORDERS

[76] Inventor: Thomas David Kehoe. 18510 Decatur Dr., Monte Sereno, Calif. 95030-3088

[21] Appl. No.: 216,630

[22] Filed: Mar. 22, 1994

[51] Int. Cl.⁶ .................................................. G10L 9/00
[52] U.S. Cl. .................................................. 704/271
[58] Field of Search ........................... 395/2.79, 2.8; 381/43

[56] References Cited

U.S. PATENT DOCUMENTS

| | | | |
|---|---|---|---|
| 4,662,847 | 5/1987 | Blum | 434/185 |
| 4,685,448 | 8/1987 | Shames et al. | 128/1 R |
| 4,784,115 | 11/1988 | Webster | 600/24 |
| 5,478,304 | 12/1995 | Webster | 600/23 |

OTHER PUBLICATIONS

Carman, B.G., Ryan G., "Electromyographic Biofeedback and the Treatment of Communicaton Disorders," in *Biofeedback: Principles and Practice of Clinicians*, edited by J.V. Basmajian, Williams & Wilkins, Baltimore, 1989, pp. 290–291.

Van Riper, C. "Stuttering: Where and Whiter?" *ASHA: A Journal of the American Speech and Hearing Association*, 1974 16:9, 483–7.

"Cafet® computer-aided fluency establishment trainer." CAFET, Inc. 4208 Evergreen Lane, Suite 213, Annandale, VA 22003.

*Primary Examiner*—David R. Hudspeth
*Assistant Examiner*—Susan Wieland

[57] ABSTRACT

A biofeedback system for speech disorders is provided which is adapted to detect disfluent speech, and to provide auditory feedback enabling immediate fluent speech, and to control the auditory feedback in accordance with the disfluent speech, to enable immediate and carryover fluency. The disfluent speech detector is preferably an electromyograph (EMG). The auditory feedback is preferably frequency-altered auditory feedback (FAF). The controller shifts the pitch of the user's voice in accordance with the user's disfluent speech. The biofeedback system may also be provided with delayed auditory feedback (DAF) which enables user control of speaking rate, with masking auditory feedback (MAP) which improves user awareness of the physical sensations of speech, and with a voice-operated switch (VOX) to switch the device off when the user stops talking. The biofeedback system may also include a timer on the DAF circuit to automatically vary the user's speaking rate at regular time intervals. The biofeedback system may also be provided with a telephone interface to enable fluent speech while talking on telephones. The system may also provide biofeedback regarding the user's vocal pitch, enabling users to speak or sing at a higher or lower pitch.

18 Claims, 9 Drawing Sheets

BIOFEEDBACK SYSTEM FOR SPEECH DISORDERS

BACKGROUND OF THE INVENTION

This invention relates, generally, to the field of speech teaching devices, and more particularly to a biofeedback system which enables persons with speech disorders, such as stuttering, to speak fluently immediately while wearing the device, and trains them to speak fluently after ceasing to use the device.

Stuttering has probably received more attention than any other speech disorder because of the way in which it dramatically exposes many of the unpleasant sides of social living. It is the dark mirror of speech, reflecting man's frustrations in communicating with his fellows. It portrays his fears of social penalties, it reveals his shame for deviancy, it is the hallmark of man's inability to communicate with his fellows.[1]

[1] Van Riper, C. *The Nature of Stuttering.* Englewood Cliffs, N.J.: Prentice-Hall, 1971.

Stuttering affects approximately 1% of children.[2] The prevalence among adults is not well-known, but 0.25% of adults is a conservative estimate. These estimates indicate that approximately 750,000 Americans stutter.

[2] Theodore Peters, Ph.D., and Barry Guitar, Ph.D., *Stuttering: An Integrated Approach to Its Nature and Treatment,* Williams & Wilkins, Baltimore, 1991.

Current treatments for stuttering are generally effective for treating children. However, current treatments are notoriously ineffective for treating adults and teenagers. Stuttering treatments often have poor carryover fluency. The person learns to speak fluently in the clinical environment, but reverts to stuttering sooner or later—sometimes as soon as he steps out of the speech-language pathologist's office. "Virtually all forms of intensive behavioral treatment for stuttering produce rather dramatic increases in fluency only to encounter serious relapse problems later."[3]

[3] Carman, B. G., Ryan, G., "Electromyographic Biofeedback and the Treatment of Communication Disorders," in *Biofeedback: Principles and Practice for Clinicians,* edited by J. V. Basmajian. Williams & Wilkins, Baltimore, 1989.

Fluency has four dimensions: continuity, rate, rhythm, and effort.[4]

[4] Theodore Peters, Ph.D., and Barry Guitar, Ph.D., *Stuttering: An Integrated Approach to Its Nature and Treatment,* Williams & Wilkins, Baltimore, 1991.

Continuity is smooth speech, or the lack of repetitions, prolongations, and blocks.

Speaking rate should be normal, about three to five syllables per second.

Rhythm means normal stress patterns, rather than monotonously stressing each syllable equally.

Fluent speech requires neither mental nor physical effort. A person who devotes full attention to speech production can't listen to another person, or generate ideas and opinions.

Fluency shaping is the most widely-used therapy for stuttering. A speech-language pathologist trains her client to speak with improved continuity, by changing rate (speaking extremely slowly), rhythm (speaking monotonously), and with concentrated mental effort. Once the client achieves this controlled fluency, he then learns to increase rate and rhythm, and reduce mental effort.

A variety of anti-stuttering devices are currently available:

Metronomes have been used to treat stuttering for about one hundred years. A metronome can improve a user's continuity, but will also slow the user's speaking rate, replace rhythm with monotony, and require concentrated mental effort. The "Pace Master" is an electronic metronome. The manufacturer (Associated Auditory Instruments, of Upper Darby, Pa.) states that the device produces no carryover fluency. The manufacturer is unsure why metronomes alter fluency, stating that the device works on "some principle possibly related to rhythmicity itself or the external cueing provided by the metronome's beat."[5]

[5] Westbrook, J., "Fluency Aids", *Letting Go: The Monthly Newsletter of the National Stuttering Project,* 1992(10).

Masking Auditory Feedback (MAF) is a system which provides a 50 Hz tone to the user's ear whenever he talks (U.S. Pat. Nos. 3,566,858 and 3,773,032). The user then can't hear his voice (or anything else). The device improves continuity without affecting rate, rhythm, or effort. MAF reduces stuttering 35%.[6] MAF requires no training. The device generally does not produce carryover fluency. MAF was developed in the 1970s. It is available from the Foundation for Fluency, of Skokie, Ill.

[6] "Effects of alterations in auditory feedback and speech rate on stuttering frequency," Kalinowsky, Armson, Roland-Mieszkowski, Stuart, and Graco, *Language and Speech,* 1993, 36, 1–16.

Delayed Auditory Feedback (DAF) is a system which delays the user's voice to his earphones by a fraction of a second. This causes the user to prolong phonated sounds, such as vowels. The user talks slower, but by removing stuttered blocks the user's overall speaking rate may actually increase. DAF also improves the user's ability to hear his voice. DAF reduces stuttering 82%.[7] Longer delays (e.g., 200 ms) often produce perfect continuity (no repetitions, prolongations, or blocks), at the expense of rate and rhythm (monotonous speech), and increased mental effort. Shorter delays (e.g., 50 ms) may have no adverse effect on rate or rhythm, and require only a little mental effort. However, short delays often have no effect on continuity, especially for persons who stutter severely. DAF requires training to use. DAF alone does not produce carryover fluency, but is usually integrated with fluency shaping therapy, which can produce carryover fluency. DAF was developed in the 1960s. It is available from Vocaltech, of Boulder, Colo.

[7] Ibid.

The "Fluency Master" (U.S. Pat. No. 4,784,115) is a device which speeds up the user's voice to his or her ear, the opposite of DAF (available from Council for Speech Development, of West Chester, Pa.). The developer "stated that he believes there is 'some kind of interference or distortion of sensory feedback' involved with stuttering. He stated that the Fluency Master provides early information to the individual regarding the vocal signal which normally passes through the skull to the ears." Studies by the developer found the device to be ineffective in conversation: "It appears that users of the device benefited most when they actively listened to the details of their voice as they talked. The burden of concentration imposed by conversation may have reduced the users' attention to their voices."[8] The Fluency Master was developed in the 1980s.

[8] Westbrook, J., "Fluency Aids", *Letting Go: The Monthly Newsletter of the National Stuttering Project,* 1992(10).

Frequency-altered Auditory Feedback (FAF) devices shift the pitch of the user's voice in his earphones higher or lower one-half octave. FAF reduces stuttering 80%.[9] FAF does not affect rate or rhythm, requires no mental effort, and requires no training to use. It causes immediate fluency—a speech-language pathologist can manually switch on FAF when a client stutters, and pull him out of the block.[10] FAF is enjoyable to use: children enjoy hearing their voices like an "alien" or a "robot," and adults find the lower pitch relaxing. However, FAF does not produce carryover fluency. FAF was developed in the 1980s. Combining FAF with DAF reduces stuttering 85%.[11]

[9] "Effects of alterations in auditory feedback and speech rate on stuttering frequency," Kalinowsky, Armson, Roland-Mieszkowski, Stuart, and Graco, *Language and Speech*, 1993, 36, 1–16.
[10] Joy Armson, Ph.D., Dalhousie University, Nova Scotia, Canada, lecture at the 1993 American Speech-Language Hearing Association convention.
[11] Ibid.

Electromyography (EMG) is a system which measures the electrical activities of muscles, through electrodes attached to the user's body. An EMG unit provides the user with auditory feedback (beeps) or visual feedback (a row of colored lights).

EMG enables user awareness and control of individual muscles. Biofeedback theory asserts that a user can control any muscle in his body if he can become aware of the muscle. Once the user establishes control, he maintains this control after ceasing to use EMG.

Biofeedback therapists often use EMG with sensory isolation, e.g., meditation, to improve user awareness of subtle physical sensations.

Placing EMG electrodes near the vocal folds "has been found to be particularly effective in directly altering laryngeal muscle activity and indirectly altering stuttering behaviors."[12] Stuttering is also associated with abnormal tension in the masseter (jaw) and other muscles.

[12] Carman, B. G., Ryan, G., "Electromyographic Biofeedback and the Treatment of Communication Disorders," in *Biofeedback: Principles and Practice for Clinicians*, edited by J. V. Basmajian. Williams & Wilkins, Baltimore, 1989.

EMG does not enable immediate fluency. The beeping earphone and flashing lights do not directly affect speech: "EMGBF [electromyograph biofeedback] must be incorporated into a treatment program, for it is not able to stand alone as an effective treatment for stuttering."[13] EMG is rarely used to treat speech disorders for this reason.

[13] Ibid.

In two studies, EMG treatment reduced stuttering 60–80%, in as little as ten 30-minute sessions. Carryover fluency was found nine months after treatment.[14]

[14] Craig, Cleary, "Reduction of stuttering by young male stutterers using EMG feedback," Biofeedback Self Regul 1982 Sep; 7(3): 241–55; Manschreck, Kalotkin, Jacobson, "Utility of electromyographic biological feedback in chronic stuttering: a clinical study with follow-up," Percept Mot Skills 1980 Oct; 51(2): 535–40.

EMG therapy is also effective with dysarthria (speech disorders caused by disturbances in muscle control) and disorders characterized by excessive laryngeal tension.[15]

[15] Carman, B. G., Ryan, G., "Electromyographic Biofeedback and the Treatment of Communication Disorders," in *Biofeedback: Principles and Practice for Clinicians*, edited by J. V. Basmajian. Williams & Wilkins, Baltimore, 1989.

Electroglottographs (EGG) record the opening and closing of a user's vocal folds. EGGs use two electrodes on the user's neck, and measure the resistance between the electrodes. This resistance changes as the vocal folds open and close. An EGG can show the frequency of the vocal folds. This is the fundamental pitch of the user's voice, without the harmonics produced by the nasal cavities, mouth, etc. One study found that "subjects demonstrated that their stuttering could be controlled by modifying the frequency of phonation intervals within short duration ranges."[16]

[16] Gow M. L., Ingham R. J. "Modifying electroglottograph-identified intervals of phonation: the effect on stuttering." J Speech Hear Res 1992 Jun; 35(3): 495–511

Kay Elemetrics, of Pine Brook, N.J., produces a computer system called "Visi-Pitch" which is similar to an electroglottograph in that it determines the user's fundamental vocal pitch. Visi-Pitch receives input only from a microphone, with no electrodes. The system's output is primarily visual, on a computer monitor. It can also provide digital output to other devices. The system is primarily used to teach deaf persons to talk.

Each of the above noted methods and systems may provide some relief for individuals who stutter. Due to the limitations associated with each system, it has been determined that the need exists for a speech disorder treatment that enables both immediate and carryover fluency, without requiring concentrated mental effort or producing abnormal-sounding speech.

SUMMARY OF THE INVENTION

Generally speaking, in accordance with the invention, a biofeedback system for speech disorders is provided. The biofeedback system detects speech disfluencies, and provides auditory feedback enabling the user to speak fluently, both immediately and with long-term carryover fluency, with minimal mental effort and/or training.

In a preferred configuration, the invention incorporates an electronic controller connected to an electromyograph (EMG) and frequency-altered auditory feedback (FAF) circuit. The controller receives data from the EMG regarding muscle tension in the user's vocal folds, masseter, and/or other speech-production muscles. The controller then controls the pitch of the FAF circuit in accordance with the user's muscle tension.

In operation, the user wears a headset with a microphone and headphones. The user also tapes three EMG electrodes onto his neck and/or jaw.

When the user speaks fluently, with his speech-production muscles relaxed, he hears his voice shifted lower in pitch. This downward shift is relaxing and pleasant, sort of like hearing James Earl Jones speak.

However, if the user tenses his speech-production muscles abnormally, prior to or during a stuttered block, he hears his voice in the headphones shifted higher in pitch. The higher pitch automatically pulls the user out of the block, with no mental effort from the user. The user's muscle tension then relaxes. If he maintains the relaxed tension, he hears his voice in his headphones dropping down to the low pitch.

The user learns (by himself or with training from a speech-language pathologist) to relax and maintain the deep vocal pitch in his headphones. When the user has learned to keep the deep vocal pitch in his headphones, he then switches the biofeedback system to a new mode. In this mode, the auditory feedback shuts off when the user's muscles are relaxed. The auditory feedback only switches on when the user's muscle tension increases. When the user has learned to keep the auditory feedback off, he can remove the headphones and continue to speak fluently. We hypothesize that he will no longer stutter.

By using a FAF circuit capable of many small shifts in pitch, the awareness of small changes in muscle tension is made possible.

The biofeedback system is not a simple combination of EMG and FAF techniques. In a combination of EMG and FAF, the FAF provides auditory feedback at a constant pitch, typically one-half octave higher than normal. While this enables immediate fluency, it does not train permanent fluency. The EMG provides visual feedback (a row of flashing lights) with no effect on fluency. To develop long-term carryover fluency, a professional therapist must train the user to understand the visual feedback, and the user must mentally concentrate on watching the visual feedback.

In contrast to a combination of EMG and FAF, the biofeedback system incorporates an electronic controller which receives input from the EMG and guides the FAF. The electronic controller uses the EMG to detect muscle tension levels. When the EMG detects abnormal muscle tension, the electronic controller alerts the user by shifting the pitch of the user's voice in his earphones. This eliminates the need for EMG visual feedback and its associated mental effort.

The biofeedback system performs functions that previously could only be done by a speech-language pathologist: perceiving when a user stutters, and providing feedback to modify the user's behavior. This innovation reduces or eliminates the training and the mental effort associated with prior therapies and technologies. The invention:

saves the time and expense of therapy, enables the user to develop fluency in daily conversations, when a speech-language pathologist can't be present, enables persons of limited mental capacity (e.g., Down's syndrome) to develop fluency.

While EMG is preferred for detecting disfluent speech, other devices can detect disfluent speech. The invention could receive data from any such device. One such device is an electroglottograph (EGG). Another device is a speech-recognizing computer programmed to recognize disfluencies.

While FAF is preferred for enabling fluent speech, many other types of auditory feedback can enable fluent speech. Masking auditory feedback (MAF), delayed auditory feedback (DAF), and a variety of digital signal processing (DSP) techniques can enable fluent speech.

These other types of auditory feedback are less effective in enabling fluency than FAF. They also are less able to convey feedback from an EMG. These types of auditory feedback could still be used with the invention, with reduced effectiveness.

A MAF masking tone is typically a 50-Hz square wave. The invention can shift this frequency in accordance with data from the EMG. Alternatively, the masking tone's waveform can change, between a pleasant sine wave to a grating square wave, for example. MAF is not as effective as FAF in enabling fluency, but it has one advantage: MAF enables sensory isolation, which improves user awareness of the physical sensations of speech.

With digital signal processing, the waveforms, harmonics, or other parameters of speech can be altered by the invention in accordance with the EMG data. Harmonizer devices used by singers currently provide fifty or more programs to change the user's voice, many without altering pitch. Any distinctive change in the user's speech in his headphones should enable the user to speak fluently, with greater or lessor effectiveness than FAF.

The invention can easily alter the delay length of a DAF circuit in accordance with the EMG data. This is considerably less effective in enabling fluent speech than FAF.

Accordingly, it is an object of the invention to provide a treatment for speech disorders that produces immediate and carryover fluency, with minimal mental effort and training.

It is another object of the invention to provide a biofeedback system for speech disorders that produces immediate and carryover fluency, with minimal mental effort and training, in combination with a system to enable auditory sensory isolation, to improve user awareness of the physical sensations of speech.

It is another object of the invention to provide a biofeedback system for speech disorders that produces immediate and carryover fluency, with minimal mental effort and training, in combination with a system that enables the user to control his or her speaking rate.

It is another object of the invention to provide a biofeedback system for speech disorders that produces immediate and carryover fluency, with minimal mental effort and training, in combination with a system that improves the user's ability to hear his voice.

It is another object of the invention to provide a biofeedback system for speech disorders that produces immediate and carryover fluency, with minimal mental effort and training, in combination with a system that produces no auditory feedback when the user is not talking.

In one embodiment of the invention, the biofeedback system automatically changes the user's speaking rate at certain time intervals. In speech therapy programs, speech-language pathologists commonly direct their clients to speak slowly for a few sentences, then speak at a normal rate for a few sentences. This improves the clients' control of their speech production muscles.

The invention incorporates a Delayed Auditory Feedback (DAF) circuit, which enables users to talk at a slower rate. An electronic timer changes the delay length every fifteen seconds. The user talks slowly for fifteen seconds, then talks at a normal rate for fifteen seconds. The delay length and the time interval are easily changed. Three or more delay lengths can be produced by adding more timers and common logic chips.

In one embodiment of the invention, the biofeedback system connects to telephones. The user hears his own voice and the received voice from the telephone in the same headphones. Many persons with speech disorders are embarrassed to wear a fluency aid in face-to-face conversations. They are comfortable using a speech aid with a telephone, however, because the listeners can't see them.

In a preferred configuration, the invention incorporates two microphones. One microphone connects directly to a telephone, and transmits the user's unaltered voice to the listener. The second microphone connects to the biofeedback system, which transmits the user's voice to his ear.

An op amp mixer combines the received voice from the telephone (the other person's voice) with the user's voice. The combined voices then go the user's headphones. A pair of Automatic Gain Control (AGC) op amps automatically balance the levels of the two voices.

In one embodiment of the invention, the biofeedback system connects to a system for detecting the user's fundamental vocal pitch, the frequency at which the user's vocal folds are vibrating. The user programs a target vocal pitch into the biofeedback system. The system compares the user's vocal pitch to the target pitch, and shifts the pitch of the FAF accordingly. This system may be used by a radio announcer to speak at a lower pitch. When his vocal pitch is too high, he hears his voice shifted lower in pitch, indicating that he should speak at a lower pitch. The desired vocal pitch can also be provided by a Musical Instrument Digital Interface (MIDI), to enable users to sing on key.

Still other objects and advantages of the invention will, in part, be obvious and will, in part, be apparent from the specification.

The invention accordingly comprises the features of construction, combinations of elements and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following descriptions taken in connection with the accompanying drawings, in which.

DETAILED DESCRIPTION OF THE PREFERRED EMBODIMENTS

Figure 1:
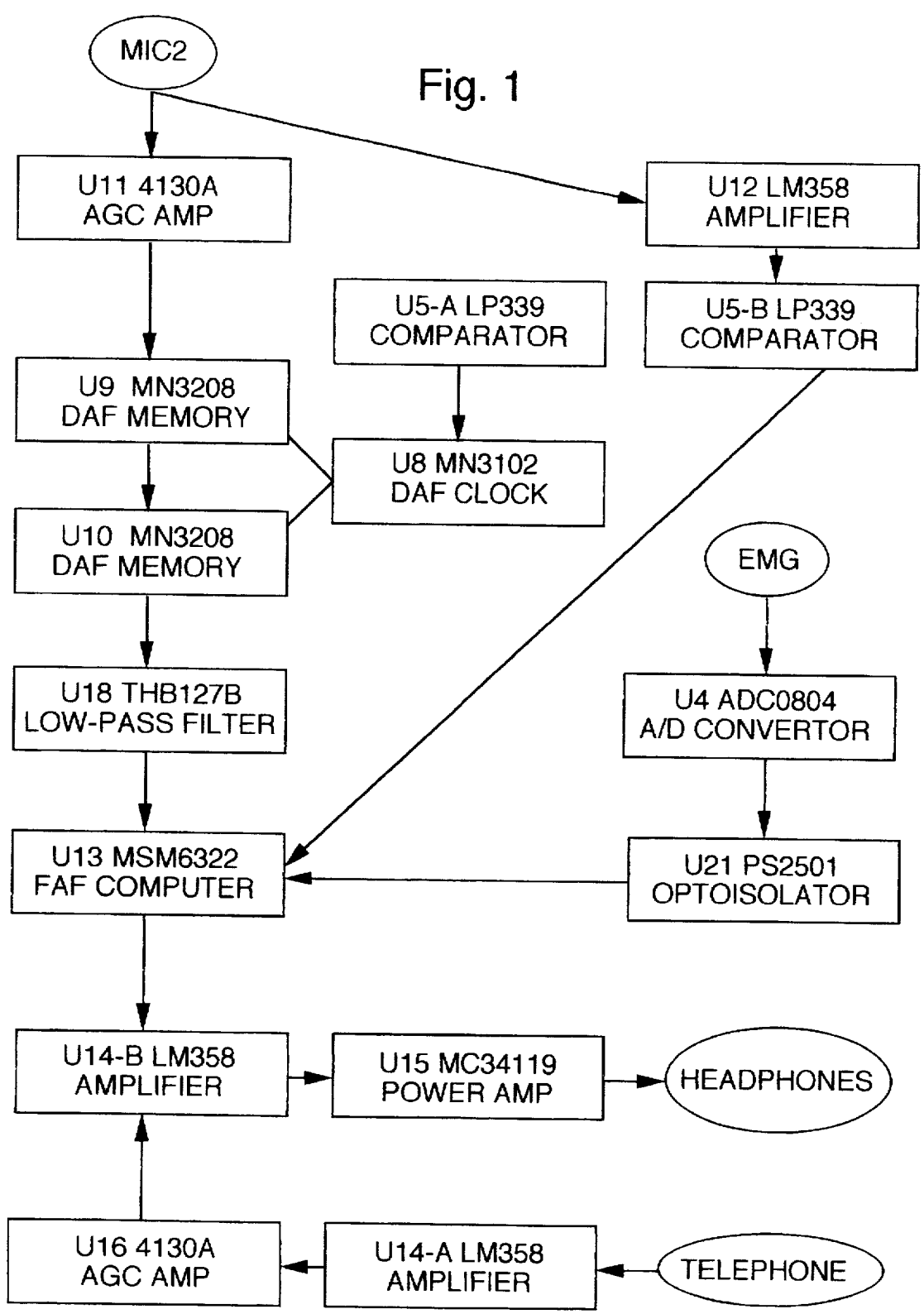
FIG. 1 is an electronic schematic diagram of a complete biofeedback system for speech disorders constructed in accordance with a preferred embodiment of the invention.

FIG. 1 shows a complete biofeedback system for speech disorders, and shows connections between the circuits shown in FIGS. 3, 4, 6, 7, and 8.

The manufacturers of the integrated circuits provide databooks showing the external parts, such as resistors and capacitors, needed to operate each chip. The capacitors and resistors are in FIGS. 1–9 are in accordance with manufacturers' preferred configurations, except as noted.

Figure 2:
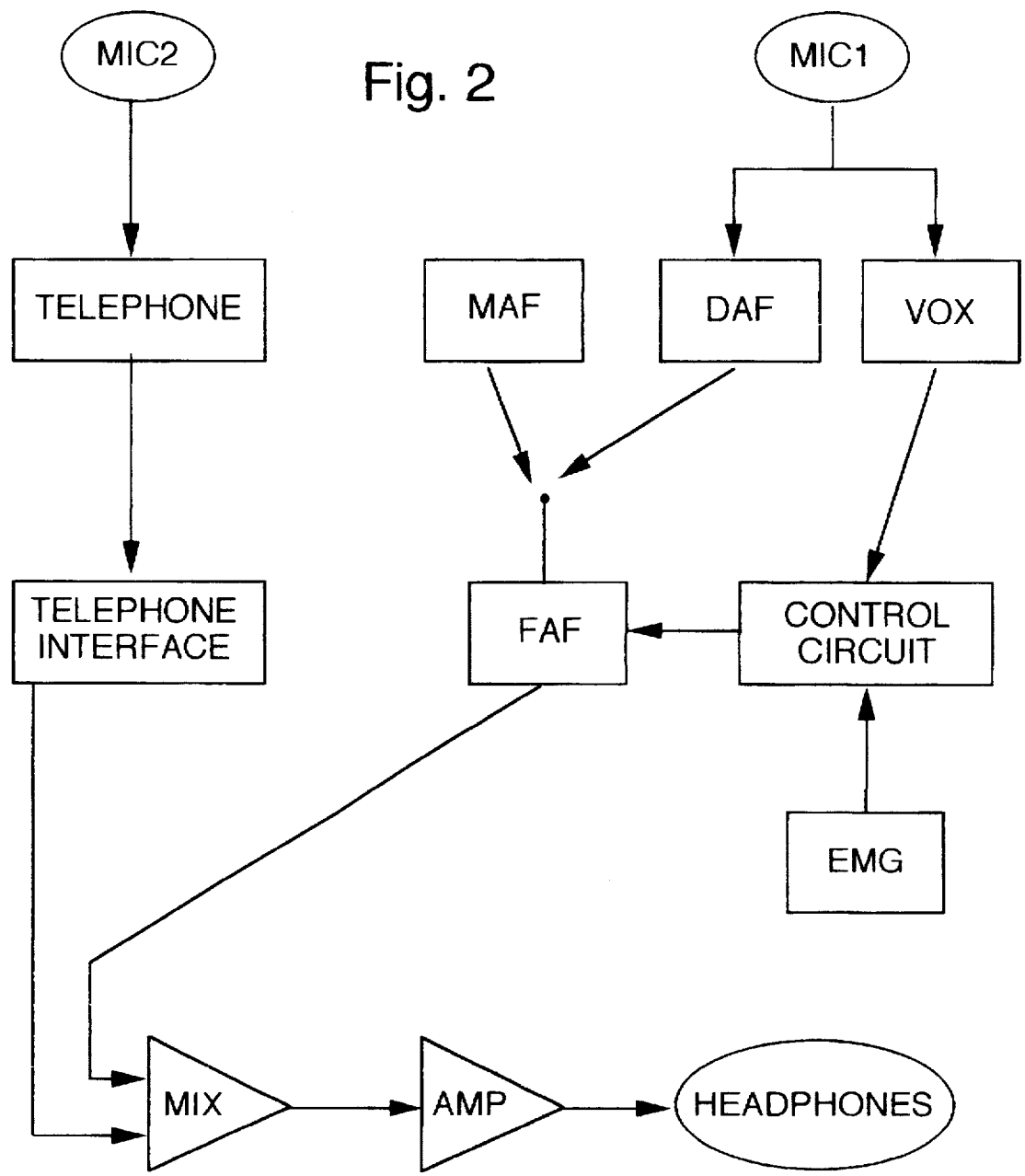
FIG. 2 is a block diagram of a complete biofeedback system for speech disorders constructed in accordance with a preferred embodiment of the invention.

FIG. 2 shows a broad overview of the biofeedback system. The user speaks into microphone (MIC1). The audio signal then goes to a voice-operated switch (VOX) and delayed auditory feedback (DAF) circuit). The user may disconnect the DAF circuit and connect a masking auditory feedback (MAF) tone generator. The chosen audio signal then go to a frequency-altered auditory feedback (FAF) circuit.

A controller circuit receives data from an electromyograph (EMG). The controller circuit controls the frequency of the FAF circuit in accordance with the data from the EMG. The controller circuit also receives data from the VOX, and powers down the FAF circuit when the user stops talking.

The user also speaks into a second microphone (MIC2). This microphone connects directly to a telephone. The received voice from the telephone (the person the user is talking to) goes to a telephone interface.

The signal from the telephone interface and the signal from the FAF are mixed by an audio mixer. The mixed signal then is amplified by an audio amplifier. Finally, the signal goes to the user's headphones.

Figure 3:
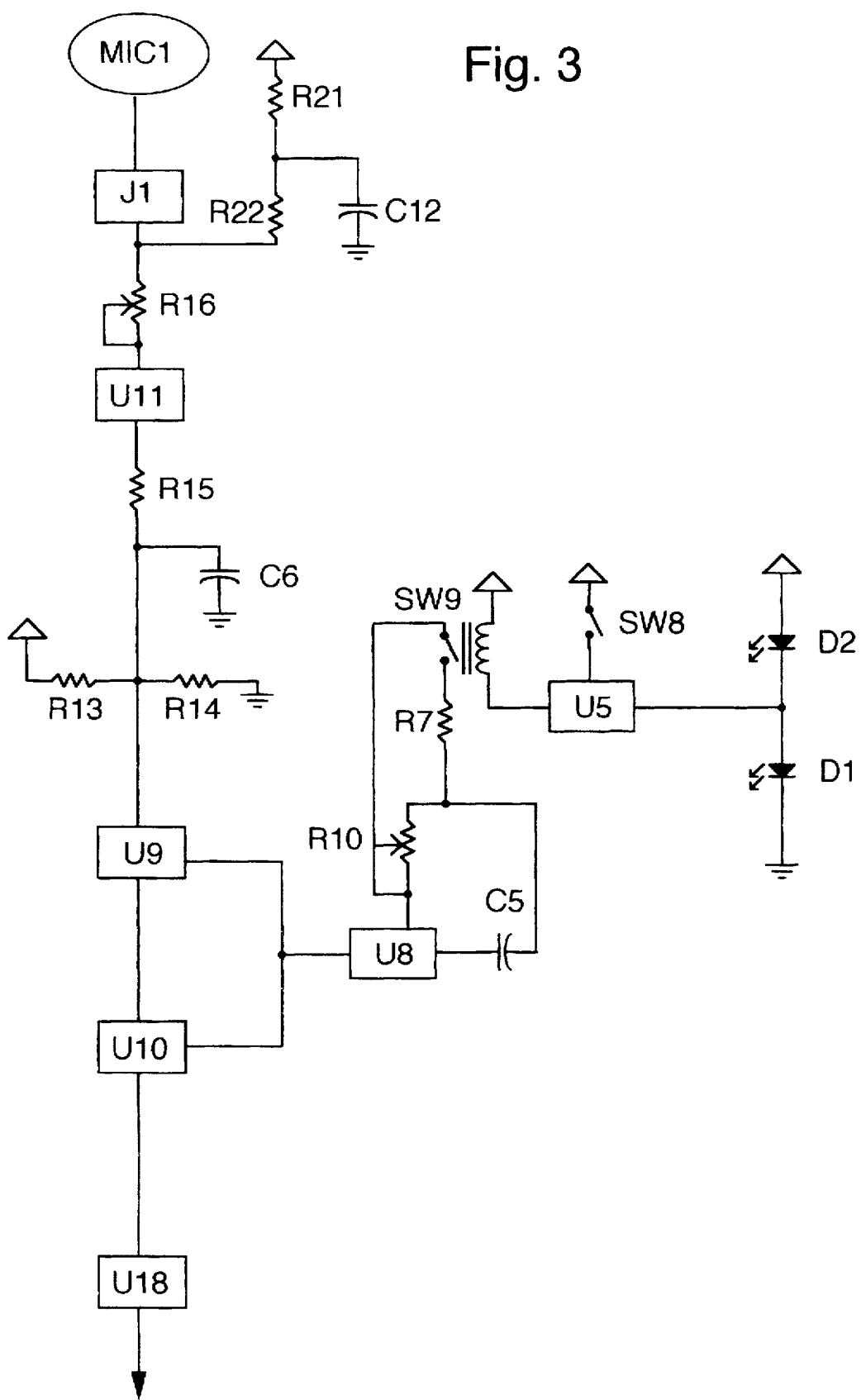
FIG. 3 is an electronic schematic diagram of a delayed auditory feedback (DAF) circuit with manual and automatic control of delay length.

FIG. 3 shows a delayed auditory feedback (DAF) circuit with manual and automatic control of delay length. Microphone (MIC1) receives the user's voice without receiving environmental noise. The microphone or microphones may be part of a headset, including headphones, worn by the user. Headsets provide excellent sound and are easy to use. The user may prefer to use a less conspicuous microphone, either on a neck band, or attached to a small earphone (such as the "Enterprise" headset made by Intel, of Santa Clara, Calif.).

The microphone should be unidirectional or bi-directional (a.k.a. noise-canceling) to reduce environmental noise. The microphone connects through jack J1, an RJ-22 type (telephone handset) jack. The microphone power is filtered to remove noise through resistors R21, R22 and capacitor C12.

Automatic gain control (AGC) op amp U11 (a GC4130, made by Gennum, of Ontario, Canada) amplifies the microphone signal to a preset voltage level. This AGC allows the user to wear the microphone close or far, or use different types of microphones, without changing auditory quality. Switch SW7 and resistors R16 and R42 improve the AGC op amp's ability to amplify the user's voice without amplifying environmental noise.

A low-pass filter (R15 and C6) removes white noise produced by the AGC op amp. The signal then is biased by R13 and R14.

The signal then enters a pair of 2K bucket brigade device (BBD) analog memory chips U9 and U10 (MN3208, made by Panasonic, of Japan). Alternatively, a single 4K MN3205 chip may be used. The BBD memory chips delay the signal, approximately 25–300 milliseconds, to provide delayed auditory feedback (DAF). BBDs are preferred for superior sound quality and simplicity of use. Digital memory may alternatively be used, for lower cost. A suitable digital delay circuit is described on page 8–24 of Analog Device's 1992 *Data Converter Reference Manual, Volume II*.

The BBD memory chips are controlled by clock U8, a Panasonic MN3102. The clock frequency determines the delay length. The clock frequency is determined by capacitor C5 and the resistance between pins 6 and 7 of clock U8. The user may set the delay at a fixed length by adjusting potentiometer R10.

Alternatively, the user may choose an automatic sequence of varying delay lengths. To do this, the user switches on switch SW8.

SW8 switches on a stable oscillator (timer) U5 (an LP339 quad comparator, with four independent circuits, made by National Semiconductor, of Sunnyvale, Calif.). The timer output changes between 0 volts and 5 volts every 15 seconds. The output is inverted by invertor U5. The inverted output switches relay SW9. When relay SW9 is on, 10K resistor R7 is connected to clock U8 pins 6 and 7. The speed of clock U8 is determined by the lowest resistance across pins 6 and 7. The user generally sets potentiometer R10 at about 50K, which produces a slow clock speed and a slow speaking rate. When relay SW9 is on, resistor R7 lowers the resistance across clock U8 pins 6 and 7, producing a faster clock speed and a normal speaking rate.

Invertor U5 also drives two light-emitting diodes (LEDs) D1 (red) and D2 (green). The red light tells the user to speak slowly. The green light indicates that the user can speak at a normal rate.

Alternatively, a three-state delay can be easily built, with an additional timer, relay, a NOR gate, and a yellow LED.

The delayed signal from the BBD memory is filtered to improve the auditory quality by 3 KHz low-pass active filter U18 (a THB 127B, made by Toko, of Japan).

Figure 4:
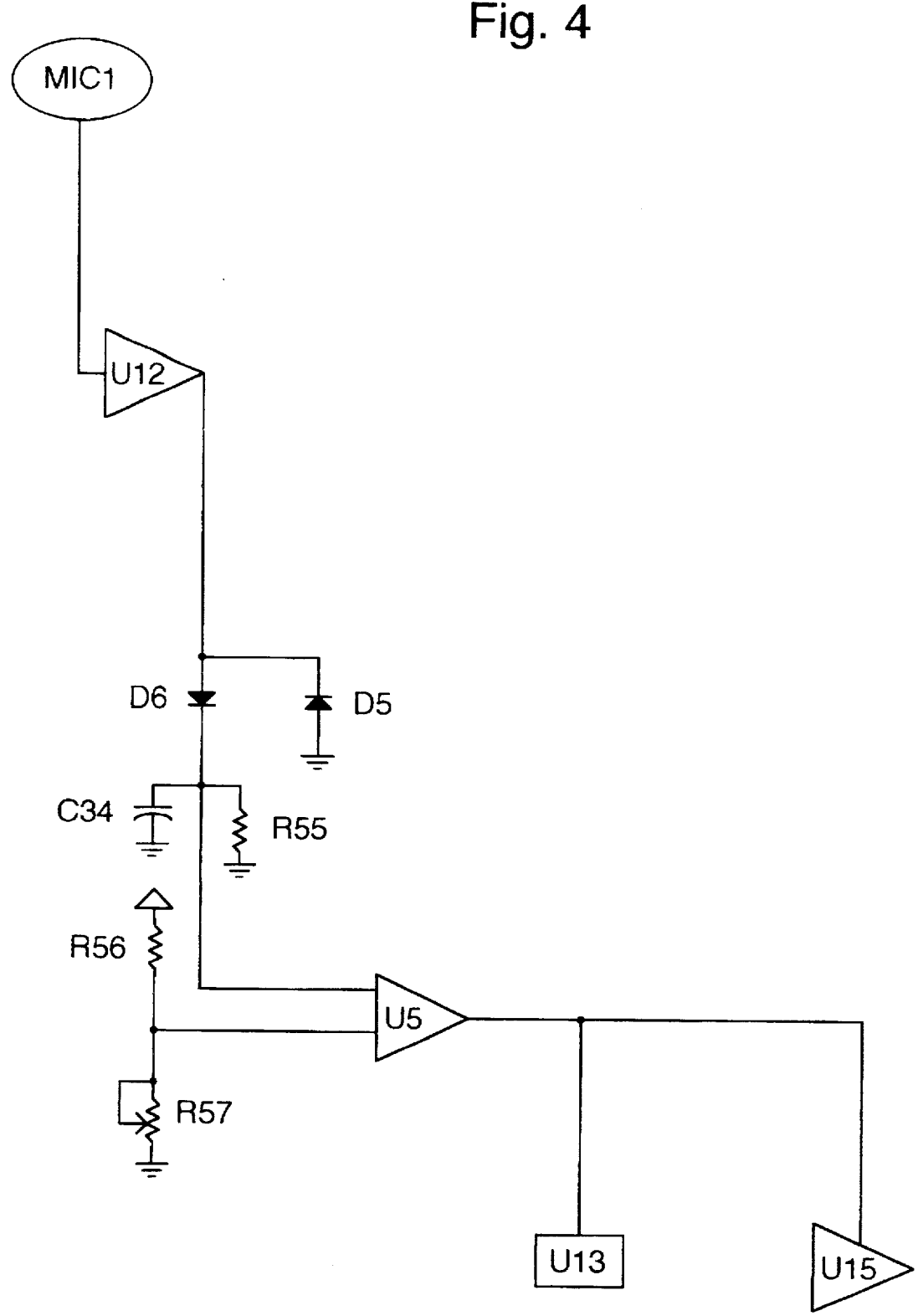
FIG. 4 is an electronic schematic diagram of a voice-operated switch (VOX)

FIG. 4 shows a voice-operated switch (VOX) circuit. This circuit operates simultaneously with the DAF circuit. A op amp U12 (half of an LM358, made by National Semiconductor) amplifies the microphone signal. Diodes D5 and D6 rectify the AC signal into DC voltage. This DC voltage then enters comparator U5 (one-fourth of the LP339 comparator). Resistors R56 and R57 provide a constant reference voltage. When the user talks, the DC voltage is greater than the reference voltage, and the comparator outputs "high." When the user stops talking, the DC voltage drops below the reference voltage, and the comparator outputs low. A timer consisting of C34 and R55 keep the DC voltage high a fraction of a second longer than the user talks, to keep the audio feedback on during short pauses. A high output from comparator U5 goes to power-down pins on the pitch control chip U13 and audio power amp U15. When the user stops talking, these chips power down. The user then hears no auditory feedback, and the battery lasts longer. The user may adjust the VOX threshold (for quiet offices vs. loud parties) by adjusting R57.

Figure 5:
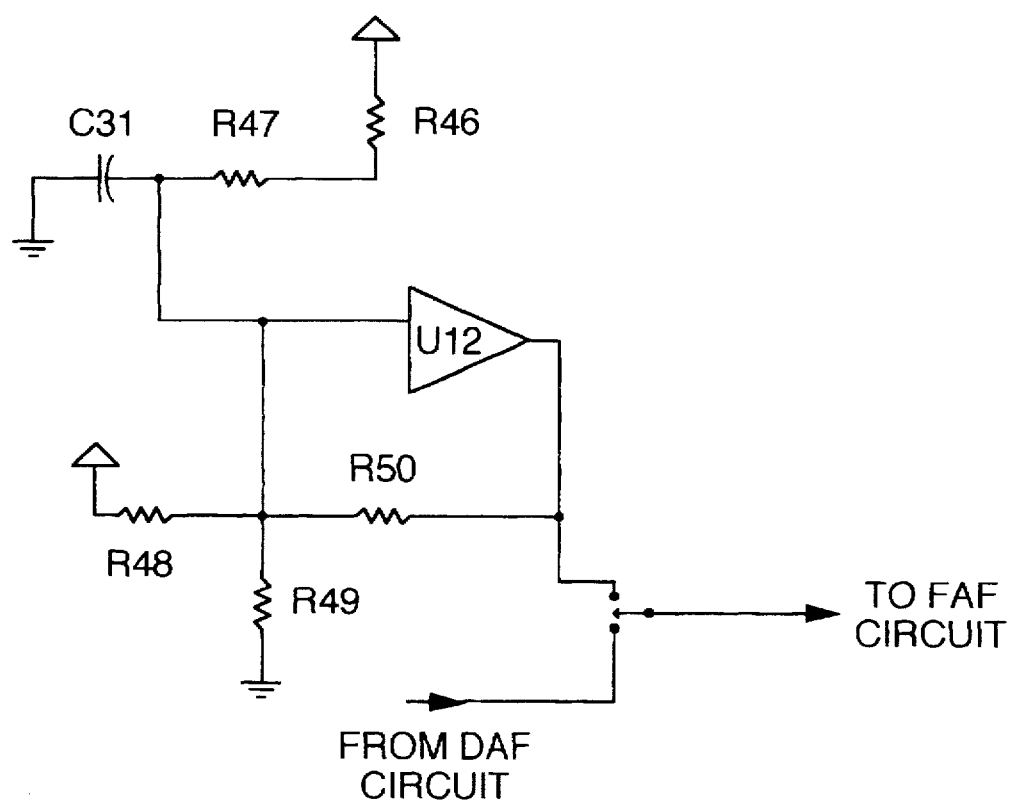
FIG. 5 is an electronic schematic diagram of a masking auditory feedback (MAF) circuit.

FIG. 5 shows a masking auditory feedback (MAF) circuit. The user may choose to hear the masking tone instead of the DAF. In this circuit, comparator U5 (one-fourth of an LP339) produces a 50 Hz square wave. A switch determines whether the user hears DAF or MAF.

Figure 6:
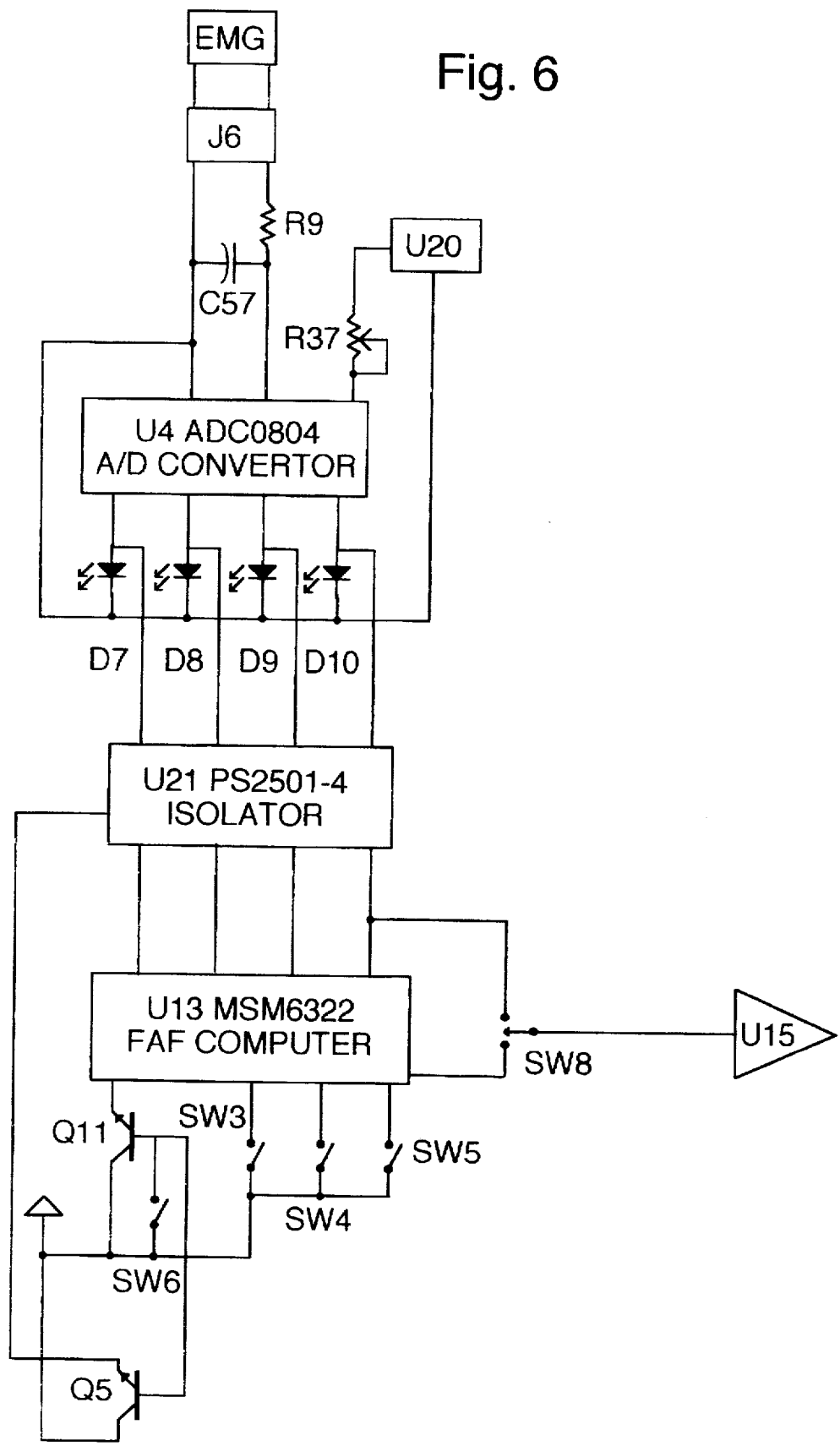
FIG. 6 is an electronic schematic diagram of an electronic controller circuit receiving data from an electromyograph (EMG) and providing frequency-altered auditory feedback (FAF) in accordance with said data received from said EMG.

FIG. 6 shows an electronic controller circuit connected to an electromyograph (EMG) and a frequency-altered auditory feedback (FAF) circuit. The signal from either the DAF or MAP circuits enters the frequency-altered auditory feedback (FAF) circuit. This circuit provides many choices of pitch, e.g., a two octave range in one-eighth octave stages, for a total of sixteen different pitches. FAF circuits are complex, comprising an analog-to-digital converter, a fast Fourier transformation, digital signal processing, and then another fast Fourier transformation and a digital-to-analog converter. The MSM6322 large-scale integration device (LSI) includes all these items (OKI Semiconductor, of Japan).

The pitch is determined by a four-bit binary number (0–15) from the controller circuit, or by may be set manually by the user with three pushbutton switches (up, down, reset to normal pitch). "Mode select" pin 6, controlled by transistor Q11, determines whether pitch control LSI U13 is in binary or pushbutton mode. Pushbutton switches SW3, SW4, and SW5 shift the pitch up, down, or back to normal. In pushbutton mode, transistor Q10 increases battery life.

In binary mode, switch SW6 switches on transistor Q5, connecting the pitch control LSI U13 to receive data from the electromyograph.

An electromyograph (EMG) measures the user's muscle tension and converts this to a 0–2.5 volt linear output. The preferred EMG is the Myotrac, made by Thought Technologies, of Montreal, Canada. The Myotrac is preferred because it uses active electrodes, which are easy for users to attach to their skin.

EMG electrode placement is discussed in the book *Biofeedback: Principles and Practice for Clinicians*, chapter 34, "Electrode Placement in Electromyographic Biofeedback," and chapter 26, "Electromyographic Biofeedback and the Treatment of Communication Disorders." (Basmajian, J. V. *Biofeedback: Principles and Practice for Clinicians*. Williams & Wilkins: Baltimore, 1989.)

The above reference shows where to place electrodes to measure tension in individual muscles. For example, the electrodes may be placed on the user's larynx, to measure vocal fold tension. This will detect stuttered voiced sounds, such as /r/ and /a/. Alternatively, the electrodes may be placed on the user's jaw to measure masseter muscle tension. This detects stuttered sounds such as /g/. Alternatively, the electrodes may be placed below the user's lips to detect stuttered sounds such as /b/ and /p/.

As an alternative to working on individual muscles, the electrodes can measure muscle tension throughout the user's neck and face. One electrode is placed on the user's neck, and the second electrode is placed on the user's jaw. The EMG then differentiates between relaxed, fluent speech, and tense, stuttered speech. This choice between narrow and broad focuses allows flexibility in treatment programs.

The EMG plugs into jack J6 (2.5 mm). The analog EMG output signal enters a memory storage device consisting of resistor R9 and capacitor C57. Stuttered blocks are generally silent, followed by a rapid relaxation in which the person produces sound (the sound may not be the desired sound—he may say "th" when he wants to say "l", and have to start the word over again). Without the memory device, the system reacts too rapidly and shifts the pitch of the silent block to a high pitch, which produces no feedback, and then shifts the relaxed sound to a lower pitch. The user receives rapidly changing, confusing feedback.

The RC memory storage device acts as a small battery. Each stuttered block charges up the battery. Each relaxed interval discharges the battery. Thus a series of stuttered blocks charges the capacitor, and the feedback pitch stays high for several seconds. Each successive stuttered block raises the pitch higher. This FAF pulls the user out of the block. It also informs the user to relax.

As the user relaxes, the feedback pitch drops. Continued relaxed speech lowers the feedback to a pleasant, deep pitch. Quick, minor disfluencies raise the feedback pitch a small increment.

The analog EMG output signal enters analog-to-digital converter U4 (an ADC0804, made by National Semiconductor) and is converted into a four-bit digital signal.

Because the biofeedback system can receive data in either analog or digital form, it can easily receive data from an electroglottograph (EGG), speech-recognition computer, or other device that detects disfluent speech, instead of receiving data from an EMG.

Four red LEDs (D7–10) enable the user to adjust potentiometer R37, labeled "THRESHOLD." The EMG output varies between electrode placements and between individuals. Potentiometer R37 corrects this. The user tenses his neck or facial muscles, and adjusts potentiometer R37 so that diodes D7–10 display the binary number 14, the highest number the FAF circuit understands.

The four-bit digital signal passes through a quad optoisolator U21 (a PS2501-4, made by Nippon Electric Company, of Japan). The optoisolator meets Food & Drug Administration (FDA) regulations to prevent electric shocks up to 5000 volts (in case lightning strikes a power line, etc.). The optoisolator consists of four LEDs and four photo transistors. The device passes data with light pulses instead of electricity. The ADC and half of the optoisolator must have their own isolated power supply (U20), including a second nine-volt battery (see below for a description of the main power supply and battery).

The EMG may additionally provide visual feedback (typically a row of green, yellow, and red lights) to the user, and/or tactile feedback (typically a small vibrating device).

Switch SW8 is used near the end of treatment programs. In the initial stages of treatment, the user hears his voice shifted down in frequency when he talks with relaxed muscle tension. When the user masters the ability to talk while keeping the auditory feedback shifted low in pitch, he then switches switch SW8. He now hears no auditory feedback when his muscle tension is relaxed. The auditory feedback is switched on when his muscle tension increases. When the user masters the ability to talk while keeping the auditory feedback off, he can remove the headphones and continue to talk fluently.

The feature works as follows: the most significant bit from the analog-to-digital converter U4 goes high (5V) only when the EMG output is in the upper half of its range (when the user's muscle tension is more than halfway between relaxed and tense). A high signal to pin 1 of the power amplifer U15 powers down the amplifier and switches off auditory feedback.

Figure 7:
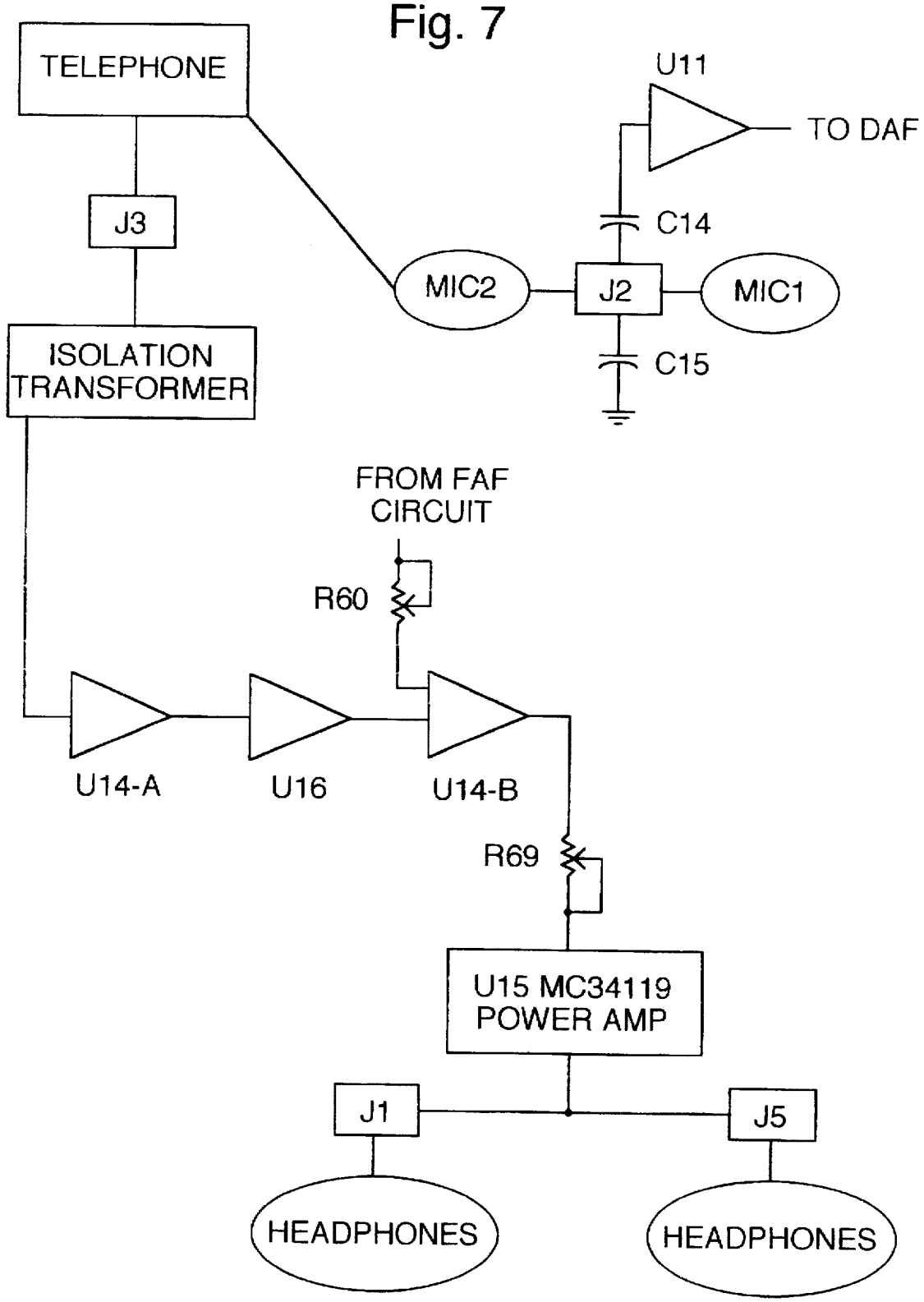
FIG. 7 is an electronic schematic diagram of a telephone interface and audio output to headphones.

FIG. 7 shows a telephone interface for the biofeedback system. The telephone interface may use either one or two microphones. Two microphones are preferred, for excellent sound. Single-microphone mode allows the user to use a standard telephone handset. The telephone connects via jack J3 (RJ-22).

Switching jack J2/SW2 (3.5 mm) switches between one- and two-microphone modes, when the user plugs in or unplugs the second microphone MIC2. In two-microphone mode, microphone MIC2 connects directly to the telephone. Microphone MIC1 connects directly to the biofeedback system. This straightforward design easily complies with Federal Communications Commission (FCC) Part 68 regulations.

In one-microphone mode, microphone MIC1 connects to the telephone through capacitors C14 and C15. The microphone also connects to the AGC U11, sending the user's voice to the DAF circuit. In an alternative configuration, a field-effect transistor (FET) op amp U12 (half of an AD822, made by Analog Devices, of Norwood, Ma.) buffers the signal from the microphone to the AGC. FET op amps have extremely high input impedances. The DAF circuit is able to receive an electrical signal from the microphone without affecting the operation of the telephone. Lower-impedance op amps may adversely affect the operation of the telephone.

The received voice from the telephone enters the biofeedback system through an audio isolation transformer, again complying with FCC Part 68 regulations. The preferred transformer has 600Ω/600Ω impedances, with 75 mW maximum power (e.g., a Magnetek 42TL016).

The signal from the transformer may be somewhat unstable, so buffer op amp U14 stabilizes the signal. Half of an LM358 (made by National Semiconductor) is preferred for its ability to handle high input currents.

A second AGC op amp U16 (a GC4130A) amplifies the signal to a preset voltage level, meeting OSHA regulations that telephone headsets may not produce more than 85 dB.

The audio mixer op amp U14 (the other half of the LM358) mixes the signal from the FAF and the signal from the telephone. Trimmer R60 allows the user to adjust the balance of the two audio signals. This balance typically sets the user's voice 8 dB louder than the received voice from the telephone. Once the balance is set, the two AGC op amps automatically maintain this balance without the user adjusting this control again.

The signal from the audio mixer then is amplified by an audio amplifier capable of driving two headphones. The preferred audio amplifier is the Motorola MC34119, which uses little power, and has a power-down pin to work with the VOX. Potentiometer R69 allows the user to adjust the volume.

The user hears the signal through binaural headphones (speakers over both ears) with wide, flat frequency range, approximately 20–20,000 Hz. An extra pair of headphones is provided for the speech therapist. The two headphones connect through jacks J1 (RJ-22) and J5 (3.5 mm).

Figure 8:
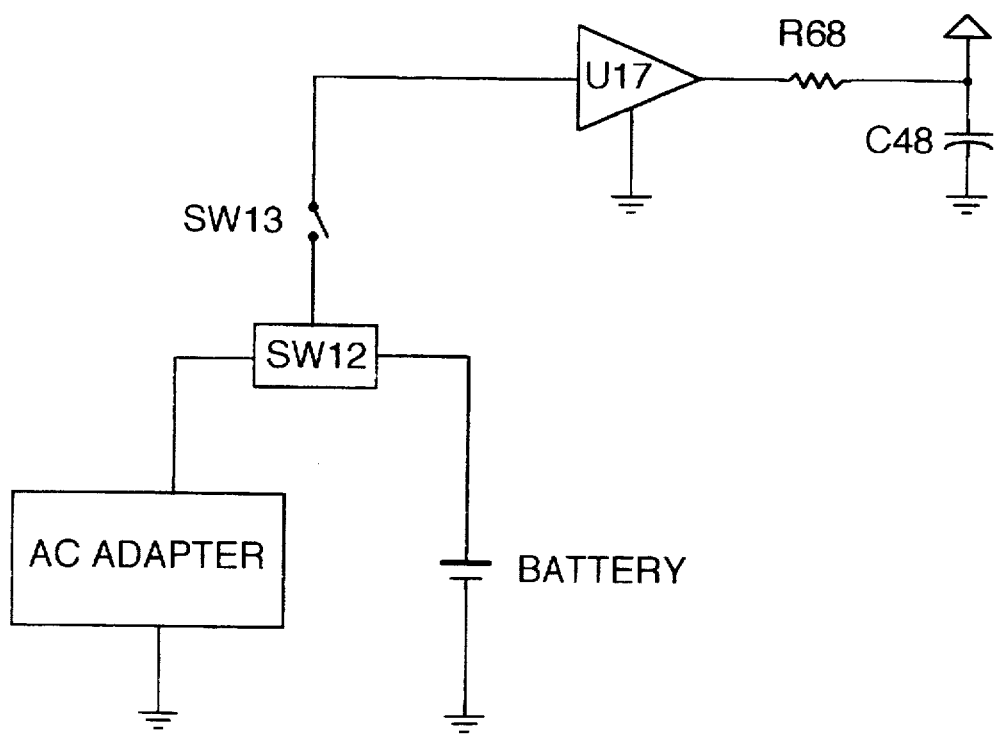
FIG. 8 is an electronic schematic diagram of the power supply circuit.

FIG. 8 shows the power supply circuit for the biofeedback system. An AC adapter converts household voltage to nine volts DC. The AC adapter should be approved by Underwriter's Laboratories (UL), such as the D9100-205-IP made by Condor, of Sunnyvale, Calif.

Unplugging the AC adapter from switching jack SW12 (2.1 mm) connects the nine-volt battery. Voltage regulator U17 reduces the input voltage (from either to AC adapter or battery) to five volts DC. The preferred voltage regulator is an LM2931Z-5.0, made by National Semiconductor. Resistor R68 and capacitor C48 filter noise from the voltage regulator.

Figure 9:
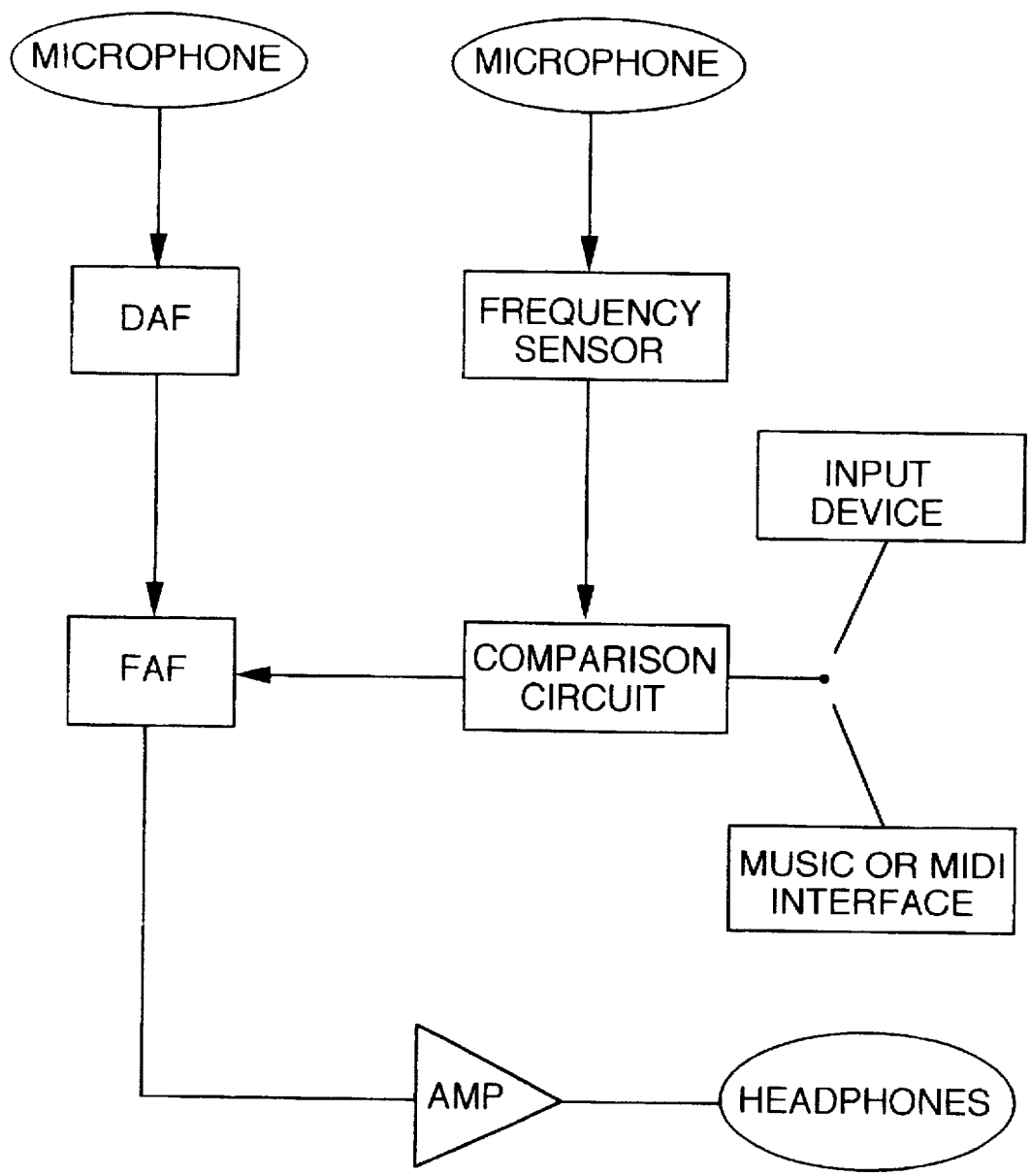
FIG. 9 is a block diagram of a vocal pitch biofeedback system.

FIG. 9 shows a vocal pitch biofeedback system. The user speaks or sings into a frequency sensor, preferably an electroglottograph or the Visi-Pitch system made by Kay Elemetrics, of Pine Brook, N.J. The user also programs a target vocal pitch into the biofeedback system, through a set of switches representing binary numbers. This target vocal pitch may alternatively come from a Musical Instrument Digital Interface (MIDI).

A simple digital comparator then compares the user's vocal pitch to the target pitch. An inverting comparator is used. The target pitch is stored as a binary number, and the Visi-Pitch output is a binary number. The comparator simply subtracts one number from the other. For example, if the target pitch is 2 (a low pitch), and the Visi-Pitch output is 4 (the user is speaking at a higher pitch), the comparator computes 2−4=−2, indicating that the user should speak lower in pitch by 2 units.

"Normal", or unaltered pitch, is an 8 in the biofeedback system. The controller receives the −2 signal from the comparator and adds this to 8. The controller then sends a "6" signal to the FAF circuit. The user hears his voice shifted down 2 one-eighth octave stages, or one-quarter octave lower, telling the user to lower his vocal pitch.

Thus, by utilizing the above construction, a biofeedback system for speech disorders can be provided which enables users to talk with immediate and carryover fluency, with minimal mental effort and/or training.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative, and not in a limiting sense.

It will also be understood that the following claims are intended to cover all of the generic and specific features of the invention, herein described, and all statements of the scope of the invention which, as a matter of language, might be said to fall therebetween.

What is claimed is:

1. A biofeedback system, comprising:

an input device for receiving information regarding a user's desired vocal pitch;

a detector for detecting said user's vocal pitch;

a comparator for comparing said desired pitch to said vocal pitch;

a frequency-altered auditory feedback (FAF) system for providing said user's voice to said user's ear, altered in pitch;

a controller for receiving data from said comparator and controlling said auditory feedback in accordance with said data from said comparator, said controller controlling the selective production of frequency-altered auditory feedback (FAF) in synchronization with said information comparing said user's vocal pitch with said user's desired vocal pitch to enable said user to alter said vocal pitch.

2. A delayed auditory feedback (DAF) system; comprising
 a delay mechanism to delay a user's voice to said user's ear;
 a plurality of a stable oscillators;
 a mechanism to vary the delay length in accordance with the oscillation intervals produced by said a stable oscillators, to alter said user's speaking rate at regular time intervals.

3. The apparatus for treating fluency disorders, comprising:
 a) means to provide fluency-enhancing auditory feedback, to immediately reduce stuttering in a user's speech;
 b) means to detect undesirable elements in said user's speech, with a biofeedback means to inform said user of said detected undesirable speech elements; and
 c) controller means which receives information from said detector means and, in response, controls said auditory feedback means, to provide the selective production of auditory feedback in synchronization with said detection of said undesirable speech elements;
 wherein said fluency-enhancing auditory feedback means comprises frequency-altered auditory feedback (FAF) thereby enabling immediate fluent speech while training said user to develop improved speech after discontinuing use of said apparatus.

4. The apparatus for treating fluency disorders, as claimed in claim 3, wherein said controller alters the degree of frequency-alteration, in response to said information.

5. The apparatus for treating fluency disorders, as claimed in claim 3, further comprising means to provide delayed auditory feedback (DAF).

6. The apparatus for treating fluency disorders, comprising:
 a) means to provide fluency-enhancing auditory feedback, to immediately reduce stuttering in a user's speech;
 b) means to detect undesirable elements in said user's speech, with a biofeedback means to inform said user of said detected undesirable speech elements; and
 c) controller means which receives information from said detector means and, in response, controls said auditory feedback means, to provide the selective production of auditory feedback in synchronization with said detection of said undesirable speech elements; thereby enabling immediate fluent speech while training said user to develop improved speech after discontinuing use of said apparatus,
 which further comprises
 d) detecting means for detecting a lack of undesirable speech elements;
 e) means to decouple said fluency-enhancing auditory feedback from said user's ear(s); and
 f) controller means which receives information from said detector means and controls said decoupling means;
 thereby decoupling said fluency-enhancing auditory feedback when said undesirable speech elements are not detected.

7. An anti-stuttering device, comprising:
 a) means to provide delayed auditory feedback (DAF);
 b) means to detect if a user is speaking; and
 c) controller means which receives information from said speech detector and uncouples said delayed auditory feedback from said user's ear(s) when said user is not speaking;
 thereby reducing stuttering in the speech of a user, without affecting said user's hearing when not speaking.

8. An anti-stuttering device, comprising:
 a) means to provide frequency-altered auditory feedback (FAF);
 b) means to detect if a user is speaking; and
 c) controller means which receives information from said speech detector and uncouples said frequency-altered auditory feedback from said user's ear(s) when said user is not speaking;
 thereby reducing stuttering in the speech of a user, without affecting said user's hearing when not speaking.

9. The anti-stuttering device, as claimed in claim 8, further comprising a means to provide delayed auditory feedback (DAF).

10. A communications device, comprising:
 a) means to provide fluency-enhancing auditory feedback, to immediately reduce stuttering in a user's speech;
 b) telephone interface means for allowing said user to communicate via said telephone, said interface means comprising transmission means for transmitting said user's voice to another person using a telephone, and receiving means for receiving another person's voice and forwarding said other person's voice to said user; and
 c) mixing means, to mix said fluency-enhancing auditory feedback with said other person's voice; and
 which provides said fluency-enhancing auditory feedback to said user's ear(s), and provides said user's voice to said other person, and provides said other person's voice to said user's ear(s), and said user hears said fluency-enhancing auditory feedback via transducer(s) that also provide said other person's voice to said user's ear(s), which reduces stuttering in the speech of a user when speaking via telephone to another person.

11. The communications device, as claimed in claim 10, wherein said fluency-enhancing auditory feedback means comprises delayed auditory feedback (DAF).

12. The communications device, as claimed in claim 10, wherein said fluency-enhancing auditory feedback means comprises frequency-altered auditory feedback (FAF).

13. The device for treating fluency disorders, as claimed in claim 12, further comprising delayed auditory feedback (DAF) means.

14. The communications device, as claimed in claim 10, wherein said fluency-enhancing auditory feedback means comprises masking auditory feedback (MAF).

15. The communications device, as claimed in claim 10, further comprising automatic balance means, to automatically balance the volume of said fluency-enhancing auditory feedback with the volume of said other person's voice.

16. An apparatus for treating fluency disorders, comprising
 a) means to provide delayed auditory feedback, to immediately reduce stuttering in a user's speech;
 b) means to detect undesirable elements in said user's speech, in which said undesirable elements characterize stuttering, with a biofeedback means to inform said user of said detected undesirable speech elements; and
 c) controller means which receives information from said detector means and, in response, automatically increases delay length when increased undesirable elements are detected which characterize severe stuttering, thereby forcing said use to speak slower, and automatically decreases delay length when reduced undesirable elements characterizing stuttering are detected, thereby allowing said user to speak at a normal speaking rate;

thereby enabling immediate fluent speech while training said user to develop improved speech after discontinuing use of apparatus.

17. An apparatus for treating fluency disorders, comprising a) means to provide fluency-enhancing auditory feedback, to immediately reduce stuttering in a user's speech;

b) means to detect myoelectric muscle electricity signals characterizing stuttering; and c) controller means which receives information from said myoelectric detector means and, in response, controls said fluency-enhancing auditory feedback means, to provide the selective production of auditory feedback in synchronization with said detection of myoelectric signals characterizing stuttering;

thereby enabling immediate fluent speech while training said user to develop improved speech after discontinuing use of apparatus.

18. An apparatus for treating fluency disorders, comprising a) means to provide fluency-enhancing auditory feedback, to immediately reduce stuttering in a user's speech;

b) means to detect changes in electrical resistance caused by said user's vocal folds opening and closing; and c) controller means which receives information from said electrical resistance detector means and, in response, controls said fluency-enhancing auditory feedback means, to provide the selective production of auditory feedback in synchronization with said detection of electrical resistance signals characterizing stuttering;

thereby enabling immediate fluent speech while training said user to develop improved speech after discontinuing use of apparatus.

* * * * *